US00PP37391P2

(12) United States Plant Patent
Li

(10) Patent No.: US PP37,391 P2
(45) Date of Patent: Apr. 28, 2026

(54) ***MANDEVILLA* PLANT NAMED 'KLEMS23101'**

(50) Latin Name: *Mandevilla sanderi*
Varietal Denomination: KLEMS23101

(71) Applicant: KLEMM + SOHN GMBH & CO. KG, Stuttgart (DE)

(72) Inventor: Ruijun Li, North Parramatta (AU)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 19/266,161

(22) Filed: Jul. 11, 2025

(51) Int. Cl.
*A01H 5/02* (2018.01)

(52) U.S. Cl.
USPC ..... Plt./232

(58) Field of Classification Search
USPC ..... Plt./232
CPC ..... A01H 6/08; A01H 5/02
See application file for complete search history.

*Primary Examiner* — Keith O. Robinson
(74) *Attorney, Agent, or Firm* — Weatherly IP Solutions, LLC; James M. Weatherly

(57) ABSTRACT

A new *Mandevilla* plant particularly distinguished by white flowers, buds with a slight pink tone, and medium compact upright plant habit, is disclosed.

1 Drawing Sheet

Genus and species: *Mandevilla sanderi.*
Variety denomination: 'KLEMS23101'.

BACKGROUND OF THE NEW PLANT

The present invention comprises a new and distinct variety of *Mandevilla*, botanically known as *Mandevilla sanderi*, and hereinafter referred to by the variety name 'KLEMS23101'. 'KLEMS23101' originated from a controlled cross-pollination conducted in October 2016 in Cobbitty, New South Wales, Australia between the proprietary female *Mandevilla* variety 'x16.35.00' (unpatented), and the proprietary male *Mandevilla* variety 'x16.16.00' (unpatented).

The seeds from the cross were sown and plants were grown for evaluation, where an individual plant designated 'KLEMS23101' was selected from the group of plants in Cobbitty, New South Wales, Australia in December 2017.

In December 2017, 'KLEMS23101' was first vegetatively propagated by vegetative cuttings in Cobbitty, New South Wales, Australia. 'KLEMS23101' was found to reproduce true to type in successive generations of asexual propagation via vegetative cuttings.

SUMMARY

The following are the most outstanding and distinguishing characteristics of this new variety when grown under normal horticultural practices in Cobbitty, New South Wales, Australia.

1. White flowers;
2. Buds with a slight pink tone; and
3. Medium compact upright plant habit.

DESCRIPTION OF THE PHOTOGRAPH

This new *Mandevilla* plant is illustrated by the accompanying photograph which shows the plant's overall plant habit including form, buds, foliage, and flowers. The photograph is of a plant approximately 13-weeks-old grown indoors in Stuttgart, Germany in May 2024. The colors shown are as true as can be reasonably obtained by conventional photographic procedures.

DESCRIPTION OF THE NEW VARIETY

The following detailed descriptions set forth the distinctive characteristics of 'KLEMS23101'. The data which define these characteristics were collected from asexual reproductions carried out in Latina, Italy. Data was collected on sixteen-week-old plants grown in 2025. Color references are to The R.H.S. Colour Chart of The Royal Horticultural Society of London (R.H.S.), 5$^{th}$ edition (2007).

Classification:
- *Family.*—Apocynaceae.
- *Botanical.*—*Mandevilla sanderi.*
- *Common.*—*Mandevilla.*
- *Designation.*—'KLEMS23101'.

Parentage:
- *Female parent.*—Proprietary Line 'x16.35.00' (unpatented).
- *Male parent.*—Proprietary Line 'x16.16.00' (unpatented).

Propagation:
- *Type.*—Cuttings.
- *Time to produce a rooted young plant.*—8 weeks.
- *Root description.*—Ovate, limited rhizome production.
- *Rooting habit.*—Normal.

Plant description:
- *Plant and growth habit.*—Upright.
- *Plant height.*—35.0 cm.
- *Plant diameter.*—20.0 cm.
- *Tendrils.*—Absent.

Lateral branch description:
- *Branching habit.*—Medium.
- *Length.*—14.0 cm.
- *Diameter.*—0.3 cm.
- *Internode length.*—5.0 cm.

*Strength*.—Strong.
*Texture*.—Smooth.
*Color*.—RHS 146C.

Foliage description:
*Arrangement*.—Opposite.
*Length*.—4.6 cm.
*Width*.—3.5 cm.
*Shape*.—Composed.
*Apex*.—Cuspidate.
*Base*.—Obtuse.
*Margin*.—Entire.
*Texture*.—Upper surface: Smooth. Lower surfaces: Smooth.
*Venation pattern*.—Pinnate.
*Color*.—Developing leaves: Upper surfaces: RHS 144A. Lower surfaces: RHS 144B. Fully expanded leaves: Upper surface: RHS 137B. Lower surface: RHS 144A.

Petioles:
*Length*.—0.4 cm.
*Diameter*.—0.15 cm.
*Texture*.—Upper surfaces: Smooth. Lower surfaces: Smooth.
*Color*.—Upper surface: RHS 141B. Lower surface: RHS 139D.

Flower description:
*Flower type and habit*.—Single, upright.
*Natural flowering season*.—Spring, summer and Autumn.
*Flower longevity on the plant*.—10 days.
*Fragrance*.—Absent.

Flowers:
*Appearance*.—Glossy.
*Diameter*.—8.3 cm.
*Length*.—5.7 cm.
*Throat diameter*.—1.7 cm.
*Tube length*.—5.5 cm.
*Tube diameter, at the base*.—0.3 cm.

Flower buds:
*Height*.—7.3 cm.
*Diameter*.—1.4 cm.
*Shape*.—Cylindrical.
*Color*.—RHS 46A.

Corolla:
*Arrangement/appearance*.—Radial, glossy.
*Petal lobe length*.—4.1 cm.
*Petal lobe width*.—3.3 cm.
*Petal lobe shape*.—Spatulate.
*Petal apex*.—Cuspidate.
*Petal margin*.—Entire.
*Petal texture*.—Upper surfaces: Smooth. Lower surfaces: Smooth. Throat texture: Rough. Throat shape: Funnel shaped. Tube texture: Rough. Color: Flower color: RHS 55B. Petal lobe: When opening: Upper surface: RHS N155C. Lower surface: RHS N155D. Fully opened: Upper surface: RHS NN155C. Lower surface: RHS N155D. Throat: RHS 185A. Tube: RHS 32B.

Sepals:
*Arrangement/appearance*.—Fused and dull.
*Length*.—1.0 cm.
*Width*.—0.25 cm.
*Shape*.—Lanceolate.
*Apex*.—Obtuse.
*Margin*.—Entire.
*Texture*.—Upper surface: Sparse pubescence. Lower surface: Sparse pubescence.
*Color*.—Inner surface: RHS 1B. Outer surface: RHS 149C.

Peduncles:
*Length*.—7.0 cm.
*Diameter*.—0.3 cm.
*Texture*.—Smooth.
*Strength*.—Strong.
*Aspect*.—About 45 degrees to axis.
*Color*.—RHS 146A.

Pedicels:
*Length*.—3.0 cm.
*Diameter*.—0.2 cm.
*Texture*.—Smooth.
*Strength*.—Strong.
*Aspect*.—About 45 degrees to axis.
*Color*.—RHS 142C.

Reproductive organs:
*Stamens*.—Quantity per flower: Five fused. Filament length: Less than 0.5 cm. Filament color: RHS 14B. Anther shape: Lanceolate. Anther size: 1.0 cm. Anther color: RHS 7C. Pollen amount: Medium. Pollen color: RHS 2D.
*Pistils*.—Quantity per flower: One. Pistil length: 3.0 cm. Stigma shape: Conical. Stigma color: RHS 7C. Style length: 2.7 cm. Style color: RHS 7C. Ovary color: RHS 144D.

Fruit and seed set: None observed.

Disease and pest/insect resistance: No disease or pest resistance observed to date.

COMPARISON WITH PARENTAL LINES AND KNOWN VARIETY

'KLEMS23101' is distinguished from its parents as described in Table 1.

TABLE 1

Comparison with Parental Lines

| Trait | Variety 'KLEMS23101' | Female parent | Male Parent |
|---|---|---|---|
| Flower colour | White | Soft pink | White |
| Bud colour | Slight pink tones | Slight pink tones | White |

'KLEMS23101' is most similar to the commercial *Mandevilla* variety 'RIO White' (not patented). Differences between the varieties are described in Table 2.

TABLE 2

Comparison with Similar Variety

| Trait | Variety 'KLEMS23101' | Commercial line 'RIO White' |
|---|---|---|
| Flowering time | Early compared to 'RIO White' | Medium, late compared to 'KLEMS23101' |

I claim:

1. A new and distinct cultivar of *Mandevilla* plant named 'KLEMS23101' as illustrated and described herein.

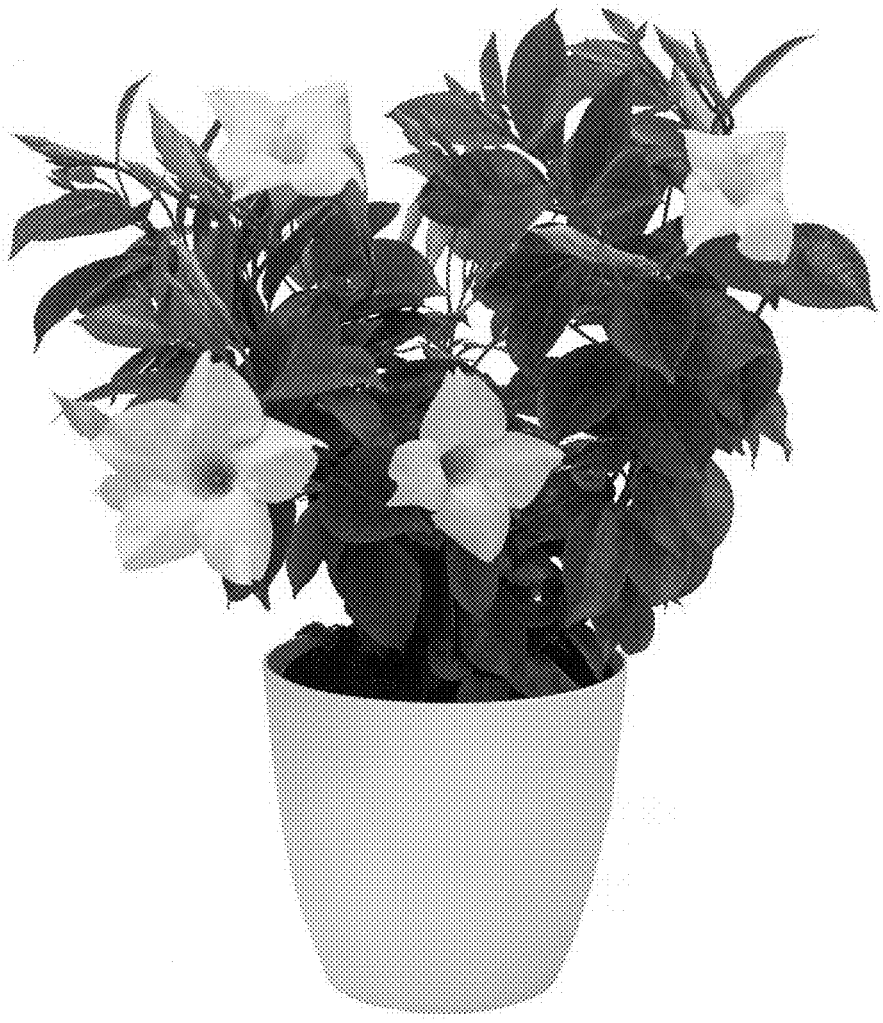

* * * * *